(12) United States Patent
Schibli et al.

(10) Patent No.: US 10,466,229 B2
(45) Date of Patent: Nov. 5, 2019

(54) SENSOR ASSEMBLY

(71) Applicant: SENSIRION AG, Stäfa (CH)

(72) Inventors: Matthias Schibli, Stäfa (CH); Daniel Lehmann, Stäfa (CH)

(73) Assignee: SENSIRION AG, Stäfa (CH)

( * ) Notice: Subject to any disclaimer, the term of this patent is extended or adjusted under 35 U.S.C. 154(b) by 0 days.

(21) Appl. No.: 15/663,275

(22) Filed: Jul. 28, 2017

(65) Prior Publication Data

US 2018/0059091 A1 Mar. 1, 2018

(30) Foreign Application Priority Data

Aug. 23, 2016 (EP) ..................... 16001844

(51) Int. Cl.
*G01N 33/487* (2006.01)
*H01L 23/31* (2006.01)
*G01N 27/12* (2006.01)

(52) U.S. Cl.
CPC ... *G01N 33/48785* (2013.01); *H01L 23/3121* (2013.01); *G01N 27/128* (2013.01); *H01L 2224/16225* (2013.01); *H01L 2924/15151* (2013.01); *H01L 2924/181* (2013.01)

(58) Field of Classification Search
CPC .......... G01N 33/48785; G01N 33/493; G01N 27/128; G01N 27/06; G01N 27/08; H01L 23/3121; H01L 23/315; H01L 2924/181; H01L 2224/16225; H01L 2924/15151
USPC ... 73/61.41, 23.3, 23.31, 23.34, 25.04, 29.1, 73/29.02, 335.01–335.09, 31.05, 31.06, 73/61.47, 715–721, 723–727, 753, 754; 29/841, 855; 600/345, 346; 422/83, 34, 422/94–97, 68.1, 82.01–82.04
See application file for complete search history.

(56) References Cited

U.S. PATENT DOCUMENTS

| 6,351,390 B1 | 2/2002 | Mayer et al. |
| 7,036,384 B2 * | 5/2006 | Tanaka .................. G01L 9/0054 73/754 |
| 7,412,894 B2 * | 8/2008 | Ueyanagi ............ G01L 19/0084 73/753 |
| 8,791,532 B2 | 7/2014 | Graf et al. |
| 2006/0263262 A1 | 11/2006 | Drbal |

(Continued)

FOREIGN PATENT DOCUMENTS

| DE | 202014105651 | 12/2014 |
| EP | 2287596 | 2/2011 |

OTHER PUBLICATIONS

Henkel Electronic Materials LLC, Safety Data Sheet "Loctite Eccobond FP4450 known as 30cc Sem Encap w/ Mylarbag 40CD", revision 003.0, issue date Jun. 22, 2017, pp. 1-7.

(Continued)

*Primary Examiner* — Robert R Raevis
(74) *Attorney, Agent, or Firm* — Mannava & Kang, P.C.

(57) ABSTRACT

A sensor assembly comprises a substrate arrangement and a sensor chip mounted to the substrate arrangement. A sensing element is integrated on or in the sensor chip and is sensitive to at least one parameter of a fluid. An access opening is provided in the substrate arrangement enabling the fluid to access the sensing element. A metallization arranged on at least a portion of the substrate arrangement seals a chamber containing the sensor chip which portion comprises one or more of a wall defining the access opening or an area facing the sensor chip.

15 Claims, 3 Drawing Sheets

(56) References Cited

U.S. PATENT DOCUMENTS

2009/0283844 A1 11/2009 Sparks
2015/0090002 A1 4/2015 Paik et al.

OTHER PUBLICATIONS

Henkel Electronic Materials LLC, Safety Data Sheet "Loctite Eccobond EO1062 known as EO1062 Quart Semicond Glob Top", revision 004.0, issue date Oct. 3, 2014, pp. 1-7.
Hysol, Technical Data Sheet "Stycast 50300-1", Feb. 2012, pp. 3.

* cited by examiner

SENSOR ASSEMBLY

PRIORITY

The present application claims priority under 35 U.S.C. 119(a)-(d) to European patent application number 16001844.6, having a filing date of Aug. 23, 2016, the disclosure of which is hereby incorporated by reference in its entirety.

TECHNICAL FIELD

The invention relates to a sensor assembly and a use of a sensor device comprising a sensor assembly.

BACKGROUND ART

Mounting a sensor chip to a substrate is required for electrically connecting the sensor chip to other components. In case that the sensor chip comprises a sensing element for sensing a parameter of a fluid, the fluid needs to access the sensing element. And third, the sensor chip is desired to be mechanically protected. However, objectives as to the arrangement of a sensor chip on a substrate may be conflicting: For example, in terms of measurement quality, and in particular in terms of response time, it may be preferred to expose the sensor chip as such to the environment and thereby granting immediate access to the fluid. Such arrangement on the other hand does promote mechanical protection of the sensor chip. An arrangement of the sensor chip in a housing may on the other hand provide a sufficient mechanical protection, however, is detrimental as to the response time since the fluid to be measured needs to travel through the housing before reaching the sensor chip.

A housing or other hard plastic protection means requires several parts to be assembled, possibly in different production processes and with demanding tolerances for providing a sufficient sealing. A rubber cap in turn would not require tight tolerances in assembly, but increases the response time of the sensor chip drastically.

In addition, it was observed by the present inventors, that many materials used for a housing or a cap, such as hard plastics or rubber, contaminate the fluid to be measured. For example, in case the fluid being a gas and the sensing element being sensitive to an analyte the quantity of which analyte is desired to be determined in the gas, the gas supplied from the outside into the housing may be contaminated by the material of the housing outgassing and impacting the fluid in its chemical composition. It was also observed that in some instances the housing rather acts as a storage for portions of the fluid, or analytes thereof: For example, in the case of humidity sensing, the housing may absorb humidity from the fluid entering the housing and thereby falsifying the measurement result, too.

DISCLOSURE OF THE INVENTION

Therefore, it is desired to provide a sensor assembly enabling a measurement with short response times and avoiding contamination of the fluid.

This problem is solved by the sensor assembly of claim 1. Accordingly, the sensor assembly comprises a substrate arrangement and a sensor chip mounted to the substrate arrangement.

The substrate arrangement may include a single substrate, two substrates, or even more substrates. Preferably, in case of more substrates, these substrates are mechanically interlinked e.g. by means of a spacer, or even by means of a further substrate. A substrate may be considered as a carrier for the sensor chip, wherein in case of multiple substrates contributing to the substrate arrangement the sensor chip preferably only is arranged on one of the multiple substrates. A substrate preferably in addition comprises conducting tracks and hence represents a circuit board. A substrate preferably is a printed circuit board with conducting tracks applied thereon and/or therein. In another embodiment, the substrate is a flexible printed circuit board.

The sensor chip preferably is a semiconductor chip, such as a silicon chip, but it may e.g. also be a glass or ceramics chip. Preferably, electronic circuitry is integrated in the sensor chip, in particular passive and/or active circuitry, such as amplifiers, filters, A/D- or D/A-converters, digital processing circuitry, etc.

The sensor chip preferably is configured to sense a parameter of a fluid. A fluid is understood as either a liquid or a gas. A parameter of the fluid may be the presence and/or concentration of a chemical analyte in the fluid, such as $CO_2$, etc. In a preferred embodiment, the sensor chip is configured to sense humidity in a gas supplied, which gas preferably may be the air surrounding the sensor assembly and/or a device the sensor assembly is mounted to/in. In the sensor chip, a sensing element is responsible for sensing the desired parameter in form of a transducer for converting the e.g. analyte into an electrical measure such as one of current, voltage, resistance, capacity, etc. Hence, the sensing element is sensitive to the one or more parameters of the fluid that is/are desired to be detected. The sensing element is integrated on or in the sensor chip. This includes, that the sensing element is attached to the sensor chip or is built from an existing portion from the sensor chip e.g. from a metal layer. The sensing element for example includes one of a polymer film sensitive to humidity, a membrane sensitive to pressure, metal oxide film sensitive to a chemical analyte. Preferably, electrodes are connected to the sensitive element, which electrodes on the other hand may be connected to circuitry integrated into the sensor chip, which circuitry may be configured to pre-process or process signals supplied by the electrodes.

The mounting of the sensor chip to the substrate arrangement may include a mechanical mounting of the sensor chip. It may additionally include an electrical mounting. Both may be achieved by means of solder bumps/balls, for example.

In order to expose the sensing element to the fluid, and in particular to a fluid of the environment of the sensor assembly such as the surrounding air, an access opening is provided in the substrate arrangement. The access opening may be embodied as a through-hole in a substrate, or in a passage between two or more substrates.

It is presently perceived that the path the fluid takes within the sensor assembly to reach the sensing element is critical to obtain reliable measurement results at a short response time. In this context, the path is considered the track for the fluid between an entrance of the access opening and the sensing element. A chamber is considered the corresponding three-dimensional space starting at the entrance of the access opening including a space in the sensor assembly the fluid can spread within and reach the sensing element. On the one hand, the path is desired to be short and the chamber is desired to be of small volume in order to allow a short response time in a measurement. On the other hand, even if the path is short and a volume of the chamber is small, components defining the path and hence the chamber may outgas or otherwise chemically react with or absorb the fluid supplied into the chamber. Hence, these components are presently perceived as possibly contaminating and/or absorbing the fluid to be measured. For example, in case the substrate is a printed circuit board containing a polymer, this polymer may outgas and change the chemical composition of the fluid. For this reason, and according to an embodiment of the present invention, it is desired to seal these components as much as possible.

For this purpose, at least a portion of the substrate arrangement is covered by a metallization. The metallization preferably is a film made from metal, such as copper used in the fabrication process which preferably is plated with gold or tin. The metallization is considered as non-permeable or at least acts as a barrier for the relevant substances ready to outgas into the chamber, or ready to be absorbed from the substrate such that the chamber representing the measuring space is sealed against such contamination and/or absorption by means of the metallization. The portion of the substrate arrangement covered by the metallization may extend across two or more substrates in case of a multi-substrate arrangement. In case of a single-substrate arrangement the metallization covers one or more areas of the substrate. Specifically, the portion of the substrate arrangement covered by the metallization comprises one or more of a wall defining the access opening or an area facing the sensor chip.

These portions are considered as critical for adversely affecting the fluid in the chamber if not sealed. Preferably, both the wall defining the access opening and an area facing the sensor chip are covered by the metallization. Not all areas facing the sensor chip need necessarily to be sealed. In a preferred embodiment, however, the wall defining the access opening and all areas of the substrate arrangement facing the sensor chip are covered by the metallization.

In addition, the metallization may serve as an ESD protection (Electro-Static-Discharge) given that it is arranged at an exposed position. In this case, the metallization may be electrically connected to a ground connection of the sensor chip and/or of the device.

In a very preferred embodiment, the substrate arrangement comprises a substrate, and preferably consists of a single substrate the sensor chip is mounted to. In such embodiment, it is preferred that the access opening comprises or is a through-hole in the substrate. Hence, the sensor chip may be mounted to a first side of the substrate, referred to as inner side, with the sensing element facing the substrate, and facing the through-hole, while the fluid to be measured is on the opposite side of the substrate, also referred to as outer side. This type of mounting is also referred to as flip-chip mounting. The front side of the sensor chip containing the sensing element, and preferably also containing integrated circuitry, faces the substrate after mounting. In order to minimize the path, it is in particular preferred that the sensor chip faces the substrate with the front side facing the through-hole. Even more preferred, the sensor chip is arranged such that the sensitive element faces the through-hole.

Preferably, the access opening consists of a single through-hole. However, in a different embodiment, the access opening may be formed by multiple through-holes in vicinity to each other, e.g. formed by means of a lattice. The through-hole preferably is made by conventional processes that are applicable to the respective kind of substrate, such as drilling, etching, laser treatment, etc. The through-hole in the substrate has one or more walls that are preferably covered by the or a portion of the metallization.

After having mounted the sensor chip to the substrate, an area of the inner side of the substrate may still face the sensor chip. Preferably, such area is also covered by a portion of the metallization, taking the form of a ring around the through-hole, which ring preferably builds a single metallization together with the metallization coverage of the wall defining the through-hole. This helps even better sealing the chamber. In a further embodiment, the metallization additionally includes a further ring around the through-hole on the outer side of the substrate, preferably also building a single metallization together with the metallization coverage of the wall defining the through-hole.

In a preferred embodiment, also a sensor chip substrate interface is sealed. Accordingly, it is preferred to provide an encapsulation to the sensor chip. Given that the sensing element shall be accessed by the fluid, it is preferred that the encapsulation does at least not cover the sensing element. In another embodiment, the entire front side of the sensor chip is uncovered by the encapsulation. Hence, the encapsulation preferably covers the backside of the senor chip, and its side walls. And, the encapsulation preferably reaches down to the substrate and therefore builds a barrier sealing a space between the substrate and the sensor chip. This prevents gases from the interior of the sensor assembly/device entering the chamber and adversely affect the measurement in form of a contamination or dilution of the fluid in the chamber.

Preferably, the encapsulation is a glob top. A glob top is understood as a drop of resin that is applied to the relevant element in liquid form and is hardened thereafter. Preferably, the material of the glob top is advantageously a resin that is crosslinked after its application to substrate 1. For example, the following material can be used: Hysol EO1062; Hysol FP4450 (Henkel); Stycast 50300 (National Starch and Chemical Company). The glob top not only protects the sensor chip as such, but also improves the mechanical connection between the sensor chip and the substrate. It also seals the chamber against the interior of the sensor assembly. No cast or mold is required for such type of encapsulation. Having applied the resin in its liquid state, e.g. on the back side of the sensor chip, the liquid extends and reaches its desired form, preferably partly supported by the substrate, before it is hardened. In other embodiments a molded plastic or a rubber cap can be used as an encapsulation to achieve a similar sealing against the inside. In another embodiment, the encapsulation is made from or includes one of an epoxy (1 or 2 component), silicone, molded plastic or rubber.

In a preferred embodiment, the substrate is a printed circuit board, either of rigid or of flexible nature. Accordingly, the substrate comprises conducting tracks and a set of contact pads. The sensor chip also comprises a set of contact pads on its first side. The set of contact pads of the sensor chip are electrically connected to the set of contact pads of the printed circuit board by means of electrically conducting material such as solder bumps. Hence, the sensor chip may be surface mounted to a printed circuit board that is prefabricated with conducting tracks and possibly with contact pads for the sensor chip and other components to be surface mounted on the printed circuit board. In another embodiment a chip-on-board configuration is possible as well.

Given that printed circuit boards often are embodied as multi-layer boards with at least one metallization layer on the front side and one on the backside, and possibly some more layers embedded in the plastics body, through-holes may be prefabricated in the printed circuit boards anyway. These through-holes are metallized, i.e. the wall defining the through-hole is covered by a metallization. While in a multi-layer board such through-hole originally is meant to electrically connect the various metal layers with each other and thereby connect components arranged on the front side of the board with components arranged on the backside thereof, such a so-called plated through-hole now is preferably misused as sealed access opening in the above context. In contrast to a through-hole serving the conventional electrical purpose, the present plated through-hole may not be electrically connected to other components but may remain isolated on a floating electrical potential.

In a further embodiment, not only a single sensor chip is arranged on the substrate, but another sensor chip is arranged on the same substrate, too, preferably flip-chip-mounted, too. This other sensor chip includes another sensing element which preferably is sensitive to the same one or more parameters the sensitive element of the first sensor chip is. Accordingly, two sensor chips are provided for measuring the same parameter in the fluid. While the first sensor chip is flip-chip mounted across the first through-hole, the other sensor chip is flip-chip mounted across a dedicated other through-hole arranged at a predefined distance from the first through-hole. When the sensor assembly is exposed to the fluid to be measured from the back side of the substrate, the fluid enters both through-holes and can be measured by both of the sensor chips. However, given that the measurement locations of the two sensor chips are different owed to the distance there between, different values may be measured for the very same parameter and may be compared. In one embodiment, an evaluation unit is provided for taking a difference between these measured values and thereby determine a local gradient of the subject parameter.

In this embodiment, the other through-hole is sealed by a dedicated metallization which is arranged on at least another portion of the substrate which other portion comprises one or more of a wall defining the other through-hole or an area facing the other sensor chip. Hence, the metallization concept may be the same as with respect to the first through-hole. In one embodiment, the metallization related to the first sensor chip is separate from the metallization related to the second sensor chip, i.e. electrically disconnected. In a different variant, the metallization related to both sensor chips is a single metallization and hence covers a wider area on the substrate.

In the above embodiments, a simple and easy way to manufacture a sensor assembly is designed by providing a bore in a substrate with a metal coating in and/or next to the bore. The bore, also referred to as through-hole, is arranged below the flip-chip mounted sensor chip and allows the fluid, such air, to reach the sensor chip, and specifically the sensing element of the sensor chip. The sensor chip is sealed by means of the metallization versus the substrate and possibly other components defining the measurement chamber, such that only the ambient at the outer side of the substrate, and hence only the humidity and/or analytes in the ambient at this outer side is measured by the sensing element.

The manufacturing of the sensor assembly with the through-hole design-in preferably relies on a single fully automated process for all critical tolerances. The sensor assembly is also mechanically much more robust. In the present sensor assembly, the combination of a small volume and a short channel results in a very fast response time.

The ease of integration becomes even more valuable for gradient measuring devices (e.g. perspiration measurement, soil humidity measurement, etc.). The distance of the two sensor chips is very well defined by the production process of the printed circuit board. The possibility of coating most of the contact area of the printed circuit board with metal in the standard PCB production process leads to minimal humidity storage effects and therefore to a very defined and fast response time.

In other embodiments, the substrate arrangement comprises two or more substrate, in particular a first substrate and a second substrate. In one embodiment thereof, the first substrate comprises the access opening in form of a through-hole. The sensor chip is arranged in a chamber between the first and the second substrate, and preferably is mounted to the second substrate. A front side of the sensor chip containing the sensitive element faces the first substrate, and in particular faces the through-hole. Here, the substrate arrangement including the two substrates and possibly a spacer in between the two substrates provides a kind of a housing to the sensor chip including the chamber the sensor chip resides in. The metallization may be provided to the first substrate in the same way the metallization is provided to the single substrate embodiments above.

In another multi-substrate embodiment, the sensor chip again is arranged in a chamber between the first and the second substrate. However, the access opening is not defined by means of a through-hole in one of the substrates. Instead, the access opening is defined by a spacing between the first and the second substrate. In case a spacer is provided between the two substrates, the spacer may not fully encircle the sensor chip. In this scenario, an area of an inner side of the first substrate facing the chamber is covered by a first portion of the metallization, and an area of an inner side of the second substrate facing the chamber is covered by a second portion of the metallization.

Preferably, the sensor assembly is part of an electronic device, be it portable such as a smart phone, or non-portable such as a measuring station. Such device is referred to as sensor device in the following. In case the device has two sensor chips according to the above embodiments, this device preferably is a sensor device for measuring a gradient of a parameter of a fluid. The sensor device may additionally comprise an evaluation circuit configured to receive a signal from the sensor element and the other sensor element and to determine the gradient of the parameter dependent on the signal from the sensor element and the other sensor element. In particular, such sensor device is used for determining a sweat rate.

According to another aspect of the present invention a method for manufacturing a sensor assembly is provided comprising the steps of generating an access opening in a substrate arrangement, generating a metallization on at least a portion of the substrate arrangement, mounting a sensor chip comprising a sensing element integrated on or in the sensor chip and sensitive to at least one parameter of a fluid to the substrate arrangement, which portion of the substrate arrangement comprises one or more of a wall defining the access opening or an area facing the sensor chip, wherein the access opening in the substrate arrangement enables the fluid to access the sensing element.

BRIEF DESCRIPTION OF THE DRAWINGS

Embodiments of the invention will be better understood and objects other than those set forth above will become apparent when consideration is given to the following detailed description thereof. Such description makes reference to the annexed drawings, wherein.

DETAILED DESCRIPTION OF THE DRAWINGS

Figure 1:
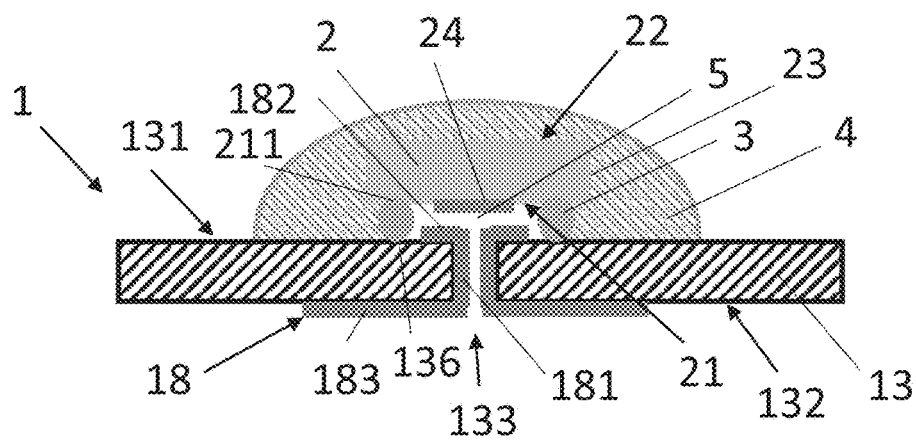
FIG. 1 shows a cut view of a sensor assembly according to an embodiment of the present invention.

FIG. 1 illustrates a cut view of a sensor assembly according to an embodiment of the present invention. In the present embodiment, a substrate arrangement 1 includes a single substrate 13, preferably in form of a printed circuit board, which may be a rigid or a flexible printed circuit board.

A sensor chip 2 is arranged on an inner side 131 of the printed circuit board. The sensor chip 2 comprises a sensing element 24 arranged at a front side 21 of the sensor chip 2. The sensor chip 2 is flip-chip mounted to the printed circuit board such that the sensing element 24 faces the inner side 131 of the printed circuit board. For doing so, a set of contact pads indicated by 211 and arranged at the front side 21 of the sensor chip 2 is electrically connected to a set of contact pads of the substrate 13, indicated by 136. The sets of contact pads 211 and 136 are connected by means of conducting material 3, e.g. by means of solder in form of a bump, or by means of other material or shape.

The substrate 13 preferably comprises conducting tracks (not shown) on the inner side 131, and preferably also on the outer side 132 opposite the inner side 131. Hence, the substrate 13 preferably serves as a mechanical carrier for the sensor chip 2, and at the same time serves for electrically connecting the sensor chip 2 to other electronics via the conducting material 3 and the conducting tracks.

The substrate 13 comprises a through-hole 133. The through-hole 133 extends through the entire thickness of the substrate 13 and opens the chamber 5 towards the outside of the sensor assembly. Hence, a fluid to be measured, which preferably is a gas present in the environment of the sensor assembly, can access the sensing element 24 through the through-hole 133.

By means of this arrangement, a chamber 5 is generated between the sensor chip 2 and the substrate 13 that has a very small volume which is advantageous for a swift response time of the sensor assembly. A path the fluid has to take from the entrance of the through-hole 133 to the sensing element 24 is short supporting the response time.

A metallization 18 arranged on portions of the substrate 13 seals the chamber 5 against outgassing of the substrate 13 and storage of humidity or analytes in the substrate 13. For this purpose, the wall/s of the through-hole 133—i.e. the vertical wall/s in the substrate 13 defining the through-hole 133—show a coverage 181 of the metallization 18. In addition, the metallization 18 includes a ring 182 around the through-hole 133 on the inner side 131 of the substrate 13 facing the sensor chip 2. This ring 182 joins the coverage 181 of the wall defining the through-hole 133. The metallization 18 may optionally include a further ring 183 around the through-hole 133 on the outer side 132 of the substrate 13. While this further ring 183 may enhance the sealing in particular in vicinity of the through-hole 133, such further ring 183 may also stem from manufacturing: The access opening in FIG. 1 may be manufactured as a plated through-hole in a conventional printed circuit board manufacturing process. Such plated thorough-holes serve as a conducting track from an inner side to an outer side in a multi-layer printed circuit board, and hence serve to electrically connect elements on the inner side to elements on the outer side. In contrast, in the present and other embodiments, such plated through-hole may be misused as sealed access opening to the sensing element of the sensor chip.

In the present embodiment, the chamber 5 is further sealed against the inside of a device the sensor assembly may be built in by means of an encapsulation in form of a glob top 4. The glob top 4 covers the back side 22 of the sensor chip 2, side walls 23 of the sensor chip 2 connecting its front side 21 with its back side 22, and covers a portion of the inner side 131 of the substrate 13. I.e., the glob top 4 reaches down to the substrate 13 and, hence, seals a space between the sensor chip 2 and the substrate 13 that is owed to the height of the conducting material 3 in between.

Figure 2:
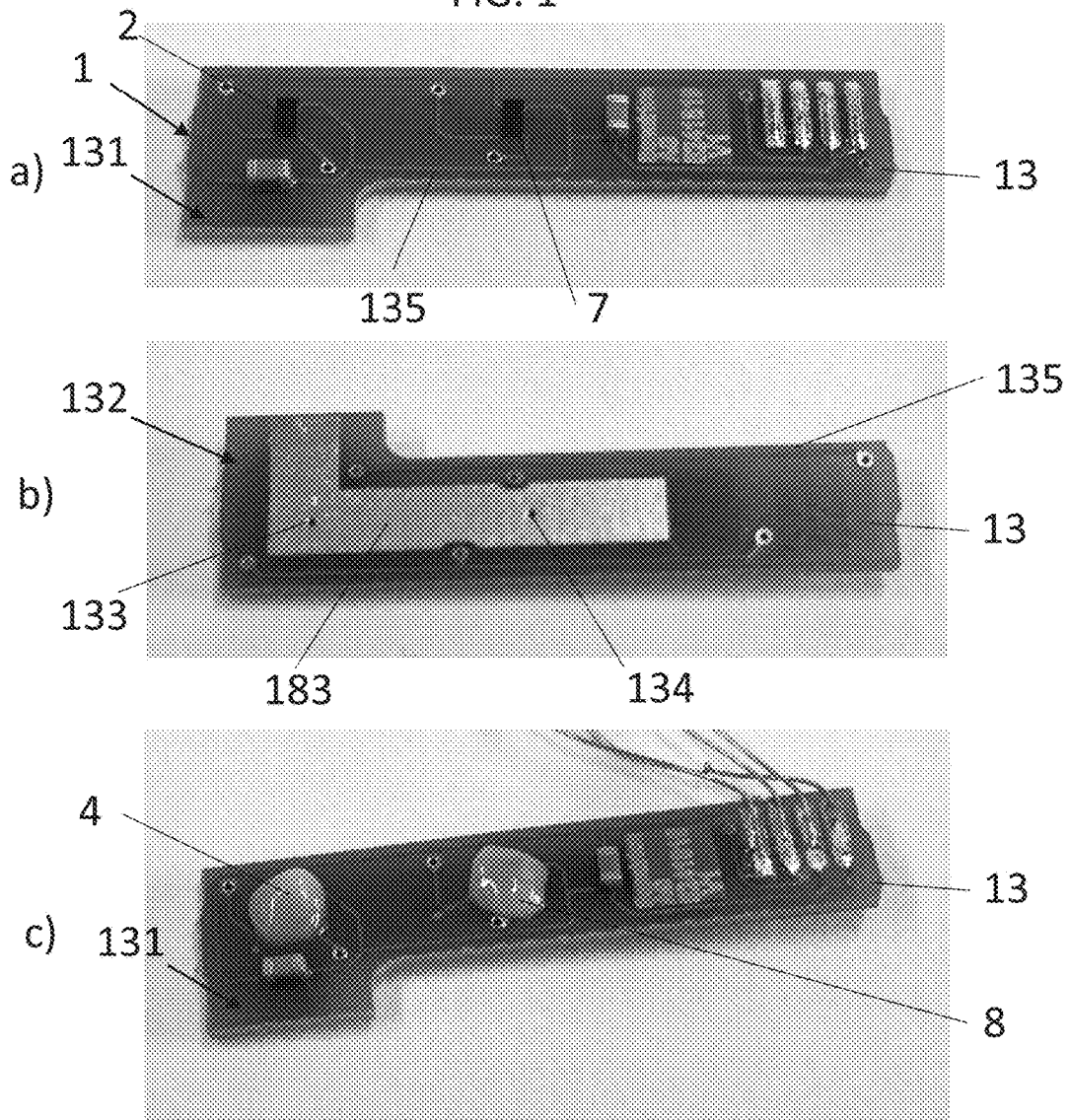
FIG. 2 illustrates a photograph of a sensor assembly according to an embodiment of the present invention, in diagram a) in top view in a first state, in diagram b) in bottom view, and in diagram c) in top view in a second state.

FIG. 2 illustrates a photograph of a sensor assembly according to an embodiment of the present invention, in diagram a) in top view in a first state, in diagram b) in a bottom view, and in diagram c) in top view in a second state. The present sensor assembly has two sensor chips 2 and 7. These sensor chips 2 and 7 are arranged at a defined distance from each other on an inner side 131 of a substrate 13 which is a printed circuit board, see top view in diagram 2a). Basically the arrangement of each sensor chip 2 and 7 follows the embodiment of FIG. 1: Hence, each sensor chip 2 and 7 is flip-chip mounted to the common substrate 13. Accordingly, each sensor chip 2 and 7 is assigned an access opening in form of a through-hole in the substrate 13, i.e. an access opening 133 in form of a through-hole, and another through-hole 134, see bottom view in diagram 2b). The sensor chips 2 and 7 are flip-chip mounted to the common substrate 13 facing the through-hole and the other through-hole 134 respectively.

Diagram 2a) illustrates a mounting state in which the sensor chips 2 and 7 are surface-mounted to the preprocessed printed circuit board, but are not encapsulated yet. This final step is illustrated in diagram 2c) in which an encapsulation in form of a glob top 4 and 8 is applied to each sensor chip 2 and 7 for sealing purposes.

According to diagram 2b), each through-hole and/or the area surrounding the through-hole 133 and 134 may be covered by a metallization. Preferably, the portion 183 of the metallization on the outer side 132 of the substrate 13 is a connected plane which is easy to manufacture.

The embodiment containing two sensor chips 2 and 7 such as shown in FIG. 2 allows for measuring gradients of a parameter of a fluid at different locations. The locations are predefined by the location coordinates of the through-holes 133 and 134 on the substrate 13. In case the sensitive elements of both sensor chips 2 and 7 are humidity sensors, a humidity flow rate can be detected by measuring the humidity values at the two distinct locations of the sensor chips 2 and 7. For example, in case such sensor assembly is arranged in proximity to human or animal skin, the evaporation of sweat, and therefore the sweat rate of this being can be measured given that one of the sensor chips 2, 7 is arranged more close to the skin while the other sensor chip 7, 2 respectively is arranged farer away than the first sensor chip 2, 7.

Figure 3:
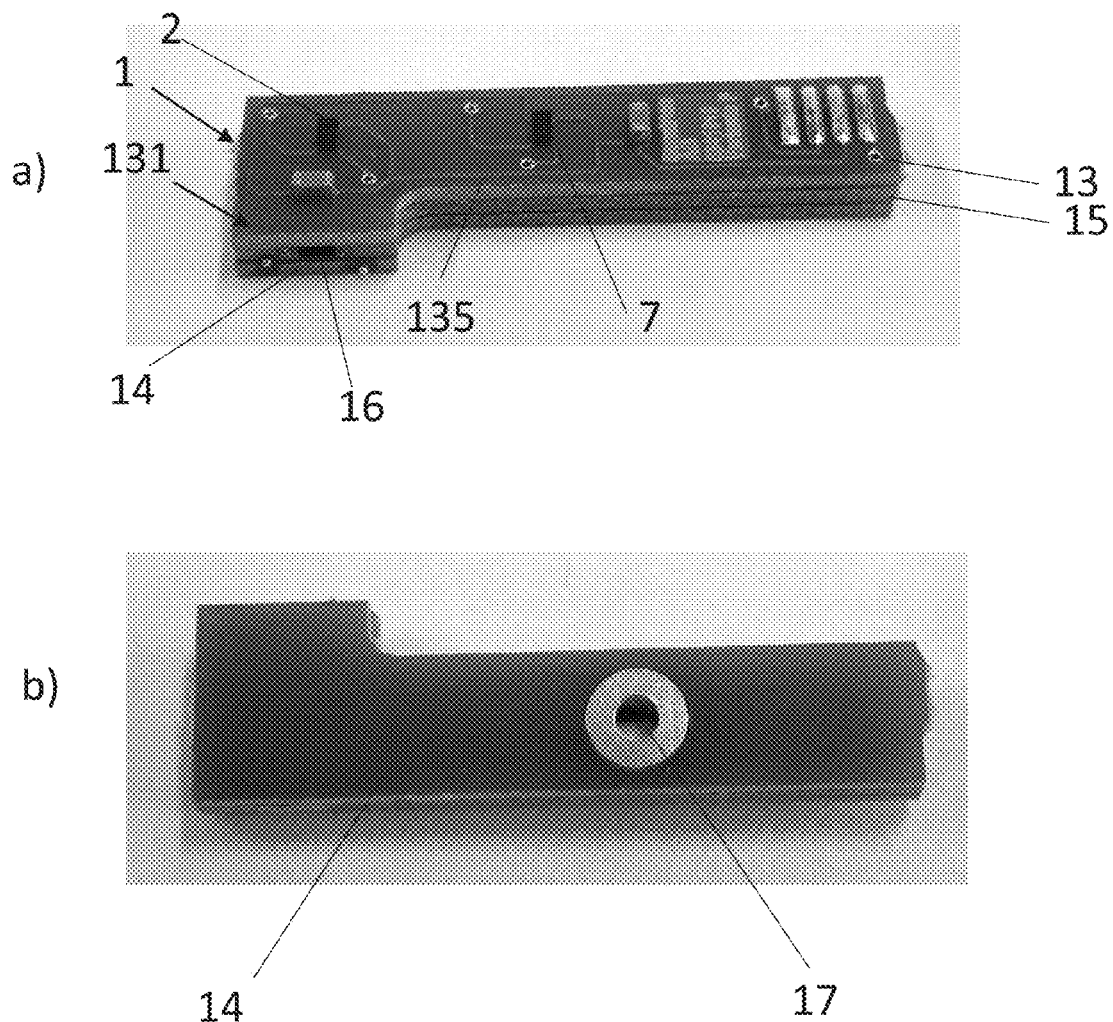
FIG. 3 illustrates a photograph of a sensor assembly according to an embodiment of the present invention, in diagram a) in a perspective view in a first state, in diagram b) in bottom view.

FIG. 3 illustrates a photograph of a sensor assembly according to another embodiment of the present invention, in diagram a) in a perspective view in a first state, in diagram b) in bottom view.

A top portion if the present sensor assembly including the substrate 13 is identical to the sensor assembly shown in FIG. 2. In addition, another substrate 14 is provided in form of a printed circuit board which is spaced from the substrate 13 by means of a spacer 15 which is also embodied as a printed circuit board. Owed to the spacer 15 and the further substrate 14, a channel 16 is generated between the substrate 13 and the other substrate 15 for conducting the fluid to the sensor chips 2 and 7. In the bottom view of diagram 3*b*), an entrance 17 for the fluid is provided in the other substrate 14 which entrance 17 leads into the channel 14. The entrance 17 in form of a through-hole in the other substrate 14 is also covered with a metallization, which may serve for sealing the channel 16 and/or serve for ESD-protection.

The sensor assembly of FIG. 3, which may be built into a housing forming a device, can be used for perspiration measurement in case the sensing elements of the two sensor chips 2 and 7 are sensitive to humidity. Here, the sensor assembly may be set with its entrance 17 onto a person's skin such that any perspiration enters into the channel 16 via the entrance 17. At the locations of the two sensor chips 2 and 7, a humidity gradient can be measured which gradient can be taken as a measure for the sweat rate of the subject person.

The embodiments of FIGS. 1-6 can also be used for other on-body/touch detections, wherein the sensor chips 2 and 7 as such are mechanically protected by means of the a small-sized through-hole 133 or a small-sized access opening 17 and the other substrate 14—channel 16 structure, if present.

Figure 4:
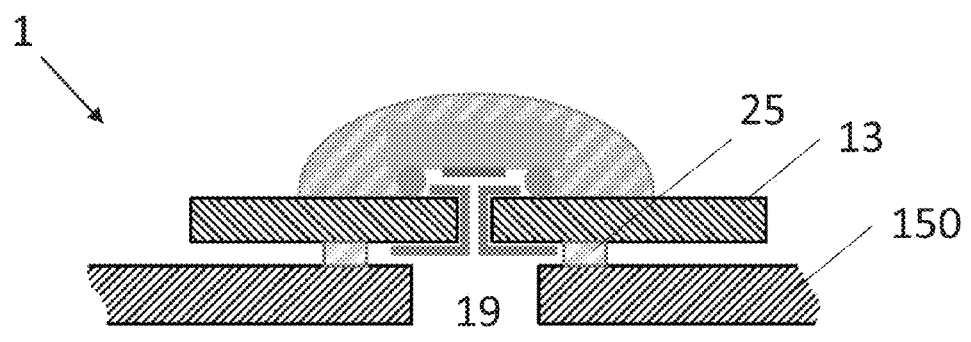
FIG. 4 shows a cut view of a sensor assembly similar to the one shown in FIG. 3.

FIG. 4 shows another embodiment of the present invention where a sensor assembly similar to the embodiment of FIG. 1 is mounted inside a sensor device 150 to measure, for example, the ambient humidity or another property of the fluid on the other side of a dividing wall of the sensor device 150, such as a housing wall. The sensor assembly, and preferably its substrate 13 is mounted to a wall of the sensor device 150, for example, preferably facing an opening 19 in the wall, with means of an adhesive substance 25 or in another embodiment with a mechanical fixture (not shown) and a sealing corresponding to the shape of the adhesive substance 25. In this embodiment, the mounting of the sensor assembly to the wall is simpler and easier than mounting the sensor chip 2 itself to the wall. In particular, no complicated molded parts are needed to seal the sensor chip 2 towards the inner side of the sensor device 150.

Figure 5:
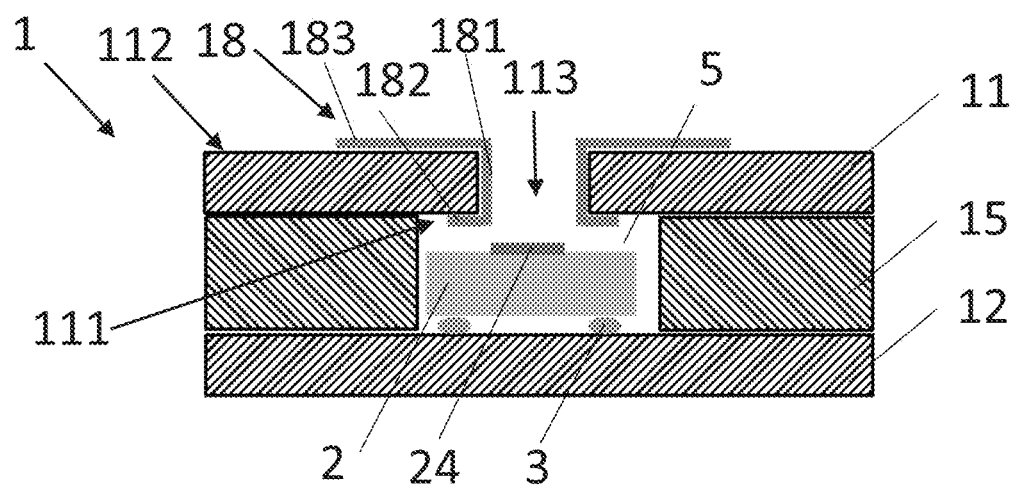
FIG. 5 shows a cut view of a sensor assembly according to further embodiment of the present invention.

FIG. 5 shows a cut view of a sensor assembly according to further embodiment of the present invention. In this embodiment, the sensor assembly comprises a substrate arrangement 1 including a first substrate 11 and a second substrate 12 arranged spaced from each other, e.g. by means of a spacer 15. The first and second substrates 11 and 12 may be of a different kind/material, or of the same kind/material. The first and second substrate 11 and 12 and the spacer 15 are arranged and designed to create a chamber 5 for the sensor chip 2. The spacer 15 encircles the sensor chip 2. The sensor chip 2 is arranged and electrically connected on/to the second substrate 12 by means of conducting material 3. Hence, the sensor chip 2 preferably is electrically connected to other components via the second substrate 12, which preferably comprises conductive tracks (not shown) for this purpose. Preferably, the second substrate 12 is a printed circuit board.

The sensitive element 24 faces a through-hole 113 in the first substrate 11 serving as access opening. The metallization 18 covers portions of the first substrate 11, similar to the embodiments of FIGS. 1 and 2: The metallization 18 includes a coverage 181 of the wall of the first substrate 11 defining the through-hole 113; additionally it partly covers an inner side 111 of the first substrate 11 facing the chamber 5 and the sensor chip 2 in form of a ring 182 around the through-hole 113; and it additionally partly covers an outer side 112 of the first substrate 11 opposite the inner side 111, preferably in from of another ring 183. Again, the access opening may be manufactured as a plated through-hole 113. Given that the electrical connection to the sensor chip 2 is performed via the second substrate 11, the first substrate 11 not necessarily needs to be a circuit board including conducting tracks except for the metallization 18.

However, in a different embodiment in connection with FIG. 5, the sensor chip 2 may also be flip-chip mounted to the first substrate 11 similar to the embodiment of FIG. 1. Here, it is preferred that the first substrate 11 is a circuit board containing conducting tracks while the second substrate 12 not necessarily requires any circuits/conducting tracks.

Figure 6:
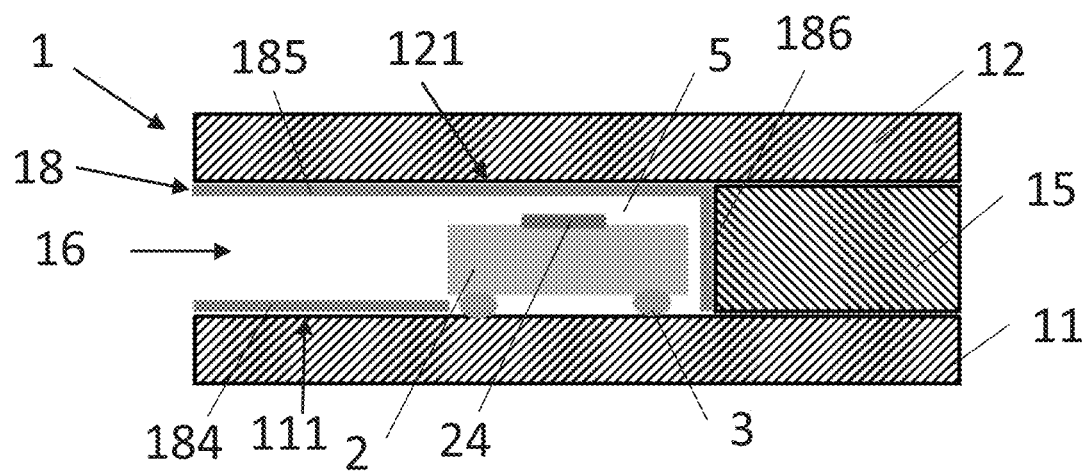
FIG. 6 shows a cut view of a sensor assembly according to further embodiment of the present invention.

FIG. 6 shows a cut view of a sensor assembly according to further embodiment of the present invention. In this embodiment, the sensor assembly again comprises a substrate arrangement 1 including a first substrate 11 and a second substrate 12 arranged spaced from each other, e.g. by means of a spacer 15. However, presently, the spacer 15 does not fully encircle the sensor chip 2. Instead, the chamber 5 for the sensor chip 2 is open to the left-hand side of FIG. 6. As a result, the access opening 16 is defined by a spacing between the first substrate 11 and the second substrate 12.

The metallization 18 now is different to the previous embodiments. Still, the metallization 18 covers portions of the first substrate 11 and the second substrate 12, i.e. portions of the substrate arrangement 1. The metallization 18 includes a first portion 184 on the first substrate 11, in particular on an inner side 111 of the first substrate 11 that co-defines the access opening 133. The metallization 18 includes a second portion 185 on the second substrate 12, and in particular on an inner side 121 of the second substrate 12 that co-defines the access opening 133.

The sensor chip 2 is arranged and electrically connected on/to the first substrate 11 by means of conducting material 3. Hence, the sensor chip 2 preferably is electrically connected to other components by means of the first substrate 11, which preferably comprises conductive tracks (not shown) for this purpose. Owed to this arrangement, the first portion 184 of the metallization 18 terminates right before the sensor chip 2 or has a similar shape as a ground plane with gaps for the conducting material 3 connecting the sensor chip 2 to the first substrate 11, while the second portion 185 on the second substrate 12 extends further into the chamber 5 and also faces the sensor chip 2. This design is preferred as to cover as much substrate surface as possible in the chamber 5 for sealing the first and second substrates 11 and 12 as best as possible. As is shown in FIG. 6, the chamber facing wall of the spacer 15 is also covered by a portion 186 of the metallization. Portion 186 may also extend to spacer walls not visible in the present cut that face other side walls of the sensor chip 2 and/or that co-define the access opening 133.

Preferably, the first substrate 11 is a printed circuit board. Given that the electrical connection to the sensor chip 2 is performed via the first substrate 11, the second substrate 12 not necessarily needs to be a circuit board including conducting tracks except for the metallization 18. However, the first and second substrates 11 and 12 may be of a different kind of material, or of the same kind of material.

The invention claimed is:

1. A sensor assembly, comprising
a substrate arrangement,
a sensor chip mounted to the substrate arrangement,
a sensing element integrated on or in the sensor chip and sensitive to at least one parameter of a fluid,
an access opening in the substrate arrangement enabling the fluid to access the sensing element, and
a metallization arranged on at least a portion of the substrate arrangement wherein the at least a portion comprises one or more of a wall defining the access opening or an area facing the sensor chip,
wherein the substrate arrangement comprises a substrate,
wherein the access opening comprises a through-hole in the substrate,
wherein the sensor chip comprises a front side on or in which the sensing element is integrated,
wherein the sensor chip is flip-chip mounted to the substrate with the front side facing the substrate, and with the front side facing the through-hole.

2. The sensor assembly of claim 1,
wherein the metallization includes a coverage of the wall defining the through-hole in the substrate.

3. The sensor assembly of claim 1,
wherein the metallization includes a ring around the through-hole on an inner side of the substrate facing the sensor chip.

4. The sensor assembly of claim 1,
wherein the metallization includes a ring around the through-hole on an outer side of the substrate opposite the inner side.

5. The sensor assembly of claim 1,
wherein the through-hole is a plated through-hole.

6. The sensor assembly of claim 5,
wherein the plated through-hole is connected to a floating electrical potential and does not electrically connect multiple layers of a circuit board.

7. The sensor assembly of claim 1,
wherein the substrate is a printed circuit board comprising conducting tracks and a set of contact pads on its inner side,
wherein the sensor chip comprises a set of contact pads on its front side,
wherein the set of contact pads of the sensor chip is electrically connected to the set of contact pads of the printed circuit board by means of electrically conducting material.

8. The sensor assembly of claim 7,
wherein the printed circuit board is a multi-layer printed circuit board.

9. The sensor assembly of claim 1, comprising
an encapsulation partly encapsulating the sensor chip,
wherein at least the sensing element remains free from the encapsulation, and
wherein the encapsulation reaches down to the substrate.

10. The sensor assembly of claim 9,
wherein the encapsulation is a glob top covering at least a back side of the sensor chip opposite the front side, and covering side walls of the sensor chip connecting the front side with the back side.

11. The sensor assembly of claim 1, comprising
another sensor chip including another sensing element integrated on or in the other sensor chip and sensitive to at least one parameter of the fluid,
another through-hole in the substrate enabling the fluid to access the other sensing element,
a metallization arranged on at least another portion of the substrate which other portion comprises one or more of a wall defining the other through-hole or an area facing the other sensor chip,
wherein the other sensor chip comprises a front side on or in which the other sensing element is integrated,
wherein the other sensor chip is flip-chip mounted to the substrate with the front side facing the substrate, and with the front side facing the other through-hole.

12. A sensor device for measuring a gradient of a parameter of a fluid, comprising
the sensor assembly according to claim 11, and
an evaluation circuit configured to receive a signals from the sensing element and the other sensing element and to determine the gradient of the parameter dependent on the signals from the sensing element and the other sensing element.

13. The sensor assembly of claim 1,
wherein the substrate arrangement comprises a first substrate and a second substrate,
wherein the access opening comprises a through-hole in the first substrate,
wherein the sensor chip is arranged between the first substrate and the second substrate,
wherein the sensor chip comprises a front side on or in which the sensing element is integrated,
wherein the sensor chip is mounted to the second substrate with the front side facing the first substrate, and with the front side facing the through-hole.

14. The sensor assembly of claim 13,
wherein the metallization includes a coverage of the wall defining the through-hole in the first substrate.

15. The sensor assembly of claim 13,
wherein in addition the metallization includes a ring around the through-hole on an inner side of the first substrate facing the sensor chip, and
wherein in addition the metallization includes a ring around the through-hole on an outer side of the first substrate opposite the inner side.

* * * * *